(12) United States Patent
Lim et al.

(10) Patent No.: US 8,888,832 B2
(45) Date of Patent: Nov. 18, 2014

(54) SYSTEM AND METHOD FOR DOUBLED USE OF PATIENT TEMPERATURE CONTROL CATHETER

(75) Inventors: Alex L. Lim, Santa Clara, CA (US); Venkata Vishnu Gurukula, Mountain View, CA (US); Jeremy T. Dabrowiak, Redwood City, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 596 days.

(21) Appl. No.: 13/247,159

(22) Filed: Sep. 28, 2011

(65) Prior Publication Data
US 2013/0079857 A1 Mar. 28, 2013

(51) Int. Cl.
*A61F 7/12* (2006.01)
*A61B 17/00* (2006.01)
*A61F 7/00* (2006.01)
*A61F 7/02* (2006.01)

(52) U.S. Cl.
CPC ....... *A61F 7/123* (2013.01); *A61B 2017/00084* (2013.01); *A61F 2007/0054* (2013.01); *A61F 2007/0056* (2013.01); *A61F 2007/0096* (2013.01); *A61F 2007/0261* (2013.01); *A61F 2007/126* (2013.01)
USPC ........................................................ 607/105

(58) Field of Classification Search
CPC .............. A61F 7/123; A61F 2007/126; A61F 2007/0054
USPC ........................................................ 607/105
See application file for complete search history.

(56) References Cited

U.S. PATENT DOCUMENTS

| 1,459,112 A | 6/1923 | Mehl |
| 1,857,031 A | 5/1932 | Schaffer |
| 2,663,030 A | 12/1953 | Dahlberg |
| 2,673,987 A | 4/1954 | Upshaw et al. |
| 3,225,191 A | 12/1965 | Calhoun |
| 3,369,549 A | 2/1968 | Armao |
| 3,425,419 A | 2/1969 | Dato |
| 3,504,674 A | 4/1970 | Swenson |
| 3,726,269 A | 4/1973 | Webster, Jr. |
| 3,744,555 A | 7/1973 | Fletcher et al. |

(Continued)

FOREIGN PATENT DOCUMENTS

| DE | 19531935 | 2/1997 |
| GB | 2040169 | 8/1980 |

(Continued)

OTHER PUBLICATIONS

Mark A. Saab, "Multi-Lumen Heat Transfer Catheter System", file history of pending U.S. Appl. No. 12/924,933, filed Oct. 8, 2010.

(Continued)

*Primary Examiner* — Linda Dvorak
*Assistant Examiner* — Kaitlyn Smith
(74) *Attorney, Agent, or Firm* — John L. Rogitz

(57) ABSTRACT

An apparatus for exchanging heat in a patient has a first elongated heat exchange catheter carrying circulating working fluid to and from a heat exchange system and a second elongated heat exchange catheter carrying circulating working fluid to and from the heat exchange system. The apparatus has a connector supporting proximal portions of both catheters while distal portions of the catheters are disposed inside a patient's vasculature to exchange heat with the patient.

17 Claims, 3 Drawing Sheets

(56) References Cited

U.S. PATENT DOCUMENTS

| | | |
|---|---|---|
| 3,751,077 A | 8/1973 | Hiszpanski |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,103,360 A | 4/1992 | Maeda |
| 5,106,360 A | 4/1992 | Ishiwara et al. |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,334,346 A | 8/1994 | Kim et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,542,928 A | 8/1996 | Evans et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,283,940 B1 | 9/2001 | Mulholland |
| 6,299,599 B1 | 10/2001 | Pham et al. |
| 6,338,727 B1 | 1/2002 | Noda et al. |
| 6,383,144 B1 | 5/2002 | Mooney et al. |
| 6,409,747 B1 | 6/2002 | Gobin et al. |
| 6,416,533 B1 | 7/2002 | Gobin et al. |
| 6,428,563 B1 | 8/2002 | Keller |
| 6,450,990 B1 | 9/2002 | Walker et al. |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaivolo et al. |
| 6,635,076 B1 | 10/2003 | Ginsburg |
| 6,679,906 B2 | 1/2004 | Hammack et al. |
| 6,685,733 B1 | 2/2004 | Dae et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,799,342 B1 | 10/2004 | Jarmon |
| 6,843,800 B1 | 1/2005 | Dobak, III |
| 6,887,263 B2 | 5/2005 | Bleam et al. |
| 6,893,419 B2 | 5/2005 | Noda et al. |
| 6,969,399 B2 | 11/2005 | Schock et al. |
| 7,189,253 B2 * | 3/2007 | Lunderqvist et al. ......... 607/105 |
| 7,241,307 B2 * | 7/2007 | Lennox ..................... 607/104 |
| 7,510,569 B2 | 3/2009 | Dae et al. |
| 7,666,215 B2 | 2/2010 | Callister et al. |
| 7,822,485 B2 | 10/2010 | Collins |
| 7,846,193 B2 | 12/2010 | Dae et al. |
| 7,857,781 B2 | 12/2010 | Noda et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,157,767 B2 * | 4/2012 | Rozenberg et al. ........ 604/98.01 |
| 8,512,280 B2 * | 8/2013 | Rozenberg et al. ........ 604/94.01 |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0049484 A1 | 4/2002 | Werneth et al. |
| 2002/0145525 A1 | 10/2002 | Friedman et al. |
| 2002/0183692 A1 | 12/2002 | Callister |
| 2002/0198579 A1 | 12/2002 | Khanna |
| 2003/0236496 A1 | 12/2003 | Samson et al. |
| 2004/0089058 A1 | 5/2004 | De Haan et al. |
| 2004/0102825 A1 | 5/2004 | Daoud |
| 2004/0210231 A1 | 10/2004 | Boucher et al. |
| 2004/0215297 A1 | 10/2004 | Collins |
| 2005/0010272 A1 | 1/2005 | Pham et al. |
| 2005/0027281 A1 * | 2/2005 | Lennox .................... 604/508 |
| 2005/0156744 A1 | 7/2005 | Pires |
| 2005/0209662 A1 * | 9/2005 | Lunderqvist et al. ......... 607/105 |
| 2007/0007640 A1 | 1/2007 | Harnden et al. |
| 2007/0076401 A1 | 4/2007 | Carrez et al. |
| 2008/0215002 A1 * | 9/2008 | Rozenberg et al. ........ 604/113 |
| 2010/0042089 A1 * | 2/2010 | Soltesz et al. .................. 606/27 |

(56) References Cited

U.S. PATENT DOCUMENTS

| | | | |
|---|---|---|---|
| 2010/0324483 A1 | 12/2010 | Rozenberg et al. | |
| 2013/0331762 A1* | 12/2013 | Kassab et al. | 604/9 |
| 2014/0094883 A1* | 4/2014 | Lim et al. | 607/106 |

FOREIGN PATENT DOCUMENTS

| | | |
|---|---|---|
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| WO | 9001682 | 2/1990 |
| WO | 9304727 | 3/1993 |
| WO | 9400177 | 1/1994 |
| WO | 9401177 | 1/1994 |
| WO | 9725011 | 7/1997 |
| WO | 9824491 | 6/1998 |
| WO | 9840017 | 9/1998 |
| WO | 0010494 | 3/2000 |
| WO | 0113809 | 3/2001 |
| WO | 0164146 | 9/2001 |
| WO | 0176517 | 10/2001 |
| WO | 0183001 | 11/2001 |

OTHER PUBLICATIONS

David J. Scott, Ben F. Brian, Lloyd F. Wright, Leo A. Chin, Edward W. Hollmen, Saniel W. Seegars, Mark A. Logan, "Apparatus and Method for Providing Enhanced Heat Transfer from a Body", file history of pending U.S. Appl. No. 12/897,637, filed Oct. 4, 2010.

Timothy R. Machold, Nicole Denise Bloom, Alex T. Roth, Dave J. Scott, Jose Alejandro, Edward A. Oliver, "Method and Apparatus for Regional and Whole Body Temperature Modification", file history of pending U.S. Appl. No. 13/101,000, filed May 4, 2011.

Timothy R. Machold, Nicole Denise Bloom, Alex T. Roth, Dave J. Scott, Jose Alejandro, Edward A. Oliver, "Method and Apparatus for Regional and Whole Body Temperature Modification", file history of pending U.S. Appl. No. 13/101,036, filed May 4, 2011.

Timothy R. Machold, Wade A. Keller, Alex T. Roth, Nicole Denise Bloom, "Method and System for Control of a Patient's Body Temperature by Way of a Transluminally Insertable Heat Exchange Catheter", file history of pending U.S. Appl. No. 13/161,648, filed Jun. 20, 2011.

F.W. Behmann, E Bontke, "Die Regelung der Wärmebildung bei künstlicher Hypothermie", Pflügers Archiv, Bd. 266, S. 408-421 (1958).

F.W. Behmann, E. Bontke, "Intravasale Kühlung", Pflügers Archiv, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

* cited by examiner

SYSTEM AND METHOD FOR DOUBLED USE OF PATIENT TEMPERATURE CONTROL CATHETER

FIELD OF THE INVENTION

The present application relates generally to patient temperature control systems.

BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present application, the above-mentioned advantages in regulating temperature can be realized by cooling or heating the patient's entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. Nos. 6,881,551 and 6,585,692 (tri-lobe catheter), U.S. Pat. No. 6,551,349 and U.S. Pat. No. 6,554,797 (metal catheter with bellows), U.S. Pat. No. 6,749,625 and U.S. Pat. No. 6,796,995 (catheters with non-straight, non-helical heat exchange elements), U.S. Pat. No. 6,126,684, U.S. Pat. No. 6,299,599, U.S. Pat. No. 6,368,304, and U.S. Pat. No. 6,338,727 (catheters with multiple heat exchange balloons), U.S. Pat. No. 6,146,411, U.S. Pat. No. 6,019,783, U.S. Pat. No. 6,581,403, U.S. Pat. No. 7,287,398, and U.S. Pat. No. 5,837,003 (heat exchange systems for catheter), U.S. Pat. No. 7,857,781 (various heat exchange catheters).

As understood herein, such catheters often cannot be customized for each individual patient when manufactured, and therefore must be made in a standard size. As further understood herein, this observation means that, in some patients, unused space may exist in the blood vessel beyond that needed to ensure adequate blood flow around the catheter.

SUMMARY OF THE INVENTION

Accordingly, an apparatus has a first elongated heat exchange catheter carrying circulating working fluid to and from a heat exchange system. The apparatus also has a second elongated heat exchange catheter carrying circulating working fluid to and from the heat exchange system. The apparatus has a connector supporting proximal portions of both catheters while distal portions of the catheters are disposed inside a patient's vasculature to exchange heat with the patient. If desired, the connector may be a Y-shaped connector.

The catheters may each have a heat exchange segment established by an elongated generally cylindrical balloon in non-limiting embodiments. Also other non-limiting embodiments, the catheters may each have at least one heat exchange segment established by a series of non-straight, non-helical links through which the working fluid flows serially from link to link. In still other non-limiting embodiments, the catheters may each have at least one heat exchange segment established by a straight central supply tube surrounded by three helical return tubes. Alternatively, the catheters may each have at least one heat exchange segment established by alternating segments of bellows regions and fluted regions, where the fluted regions have helical flutes in non-limiting embodiments.

However, it is to be understood that the heat exchange segments may be combined in a single embodiment such that one catheter may have one of the above-described heat exchange segments while the other catheter may have another of the above-described heat exchange segments. It is to be further understood that, in non-limiting embodiments, both catheters may have substantially similar heat exchange segments as described above. Even further, it is to be understood that each catheter May have more than one heat exchange segment, where the plural heat exchange segments of a single catheter may be any of the above-described segments without limitation.

In another aspect, a method includes providing a first elongated heat exchange catheter carrying circulating working fluid to and from a heat exchange system. The method also includes providing a second elongated heat exchange catheter carrying circulating working fluid to and from the heat exchange system. Last, the method includes using a connector supporting proximal portions of both catheters and disposing distal portions of the catheters inside a patient's vasculature to exchange heat with the patient.

In still another aspect, a system includes plural elongated heat exchange catheters carrying circulating working fluid to and from a heat exchange system. The system also includes a connector supporting proximal portions of the catheters while distal portions of the catheters are disposed inside a patient's vasculature to exchange heat with the patient.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
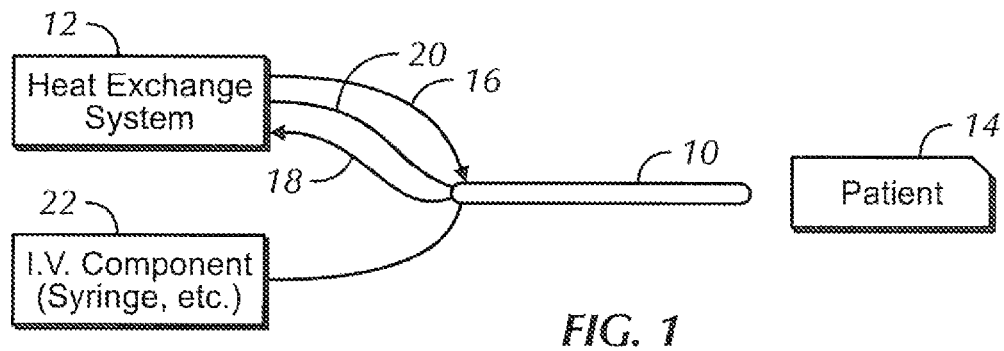
FIG. 1 is a schematic diagram showing an example catheter engaged with an example heat exchange system.

Referring initially to FIG. 1, an intravascular temperature management catheter 10 is in fluid communication with a catheter temperature control system 12 that includes a processor executing logic described in one or more of the patents referenced herein to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as but not limited to saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., patient suffering from sub-arachnoid hemorrhage or intracerebral hemorrhage.

As shown, working fluid may be circulated between the heat exchange system 12 and catheter 10 through supply and return lines 16, 18 that connect to the proximal end of the catheter 10 as shown. Note that as used herein, "proximal" and "distal" in reference to the catheter are relative to the system 12. A patient temperature signal from a catheter-borne temperature sensor may be provided to the system 12 through an electrical line 20 or wirelessly-if desired. Alternatively, a patient temperature signal may be provided to the system 12 from a separate esophageal probe or rectal probe or tympanic sensor or bladder probe or other temperature probe that measures the temperature of the patient 14.

The catheter 10, in addition to interior supply and return lumens through which the working fluid is circulated, may also have one or more infusion lumens connectable to an IV component 22 such as a syringe or IV bag for infusing medicaments into the patient, or an instrument such as an oxygen or pressure monitor for monitoring patient parameters, etc.

The catheter 10 can be positioned typically in the vasculature of the patient 14 and more preferably in the venous system of the patient 14 such as in the inferior vena cava through a groin insertion point or the superior vena cava through a neck (jugular or subclavian) insertion point.

Figure 2:
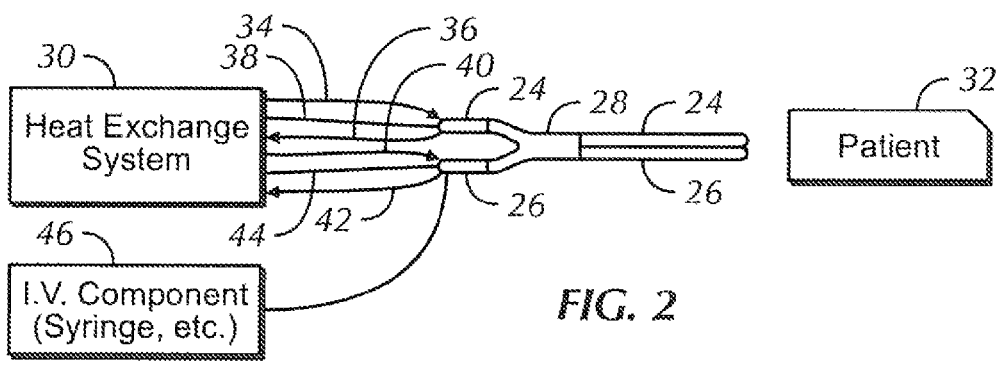
FIG. 2 is a schematic diagram of two catheters advanced in concert with each other through a Y-connector and having distal portions to be disposed in a patient.

Now in reference to FIG. 2, a schematic diagram of two catheters such as two of the catheters 10 shown in FIG. 1, can be advanced in concert with each other through, e.g., a Y-connector and having distal portions/ends to be disposed in a patient is shown. A first elongated heat exchange catheter 24 and a second elongated heat exchange catheter 26 are in fluid communication with a catheter temperature control system 30. A Y-connector 28 is also shown in FIG. 2, the Y-connector 28 supporting proximal portions of both the catheters 24 and 26. It is to be understood that the control system 30 includes a processor executing logic described in one or more of the patents referenced herein to control the temperature of working fluid circulating through the catheters 24 and 26 in accordance with a treatment paradigm responsive to patient core temperature feedback signals.

In accordance with present principles, the catheters 24 and 26 can be used to induce therapeutic hypothermia in a patient 32 using the catheter, in which coolant such as, but not limited to, saline circulates in closed loops as similarly described in reference to FIG. 1. The catheters 24 and 26 can also be used to warm a patient in accordance with present principles. Regardless, it is to be appreciated that the plural catheters of FIG. 2 can more effectively and efficiently cool or warm the patient 32 when advanced into the patient 32 in concert at the same insertion site than can a single catheter.

Still in reference to FIG. 2, working fluid may be circulated between the heat exchange system 30 and the catheters 24 and 26 through respective supply and return lines 34 and 36 (for the catheter 24) and 40 and 42 (for the catheter 26), thereby providing fluid to both catheters 24 and 26. As may be appreciated from FIG. 2, the Y-connector 28 supports proximal portions of the catheters 24 and 26. Thus, the catheters 24 and 26 may enter the divided end of the Y-connector 28, extend through respective arms of the Y-connector 28, and closely exit the other end of the Y-connector 28 such that distal portions of the catheters 24 and 26 may be disposed in concert into the patient 32 to exchange heat with the patient. It may be appreciated that the Y-connector 28 serves to stabilize the catheters 24 and 26 in, close juxtaposition to each other. Not that as used herein, "proximal" and "distal" in reference to the catheters 24 and 26 are relative to the system 30.

Additionally, patient temperature signals from catheter-borne temperature sensors may also be provided to the system 30 through respective electrical lines 38 and 44, or wirelessly if desired, such that the electrical lines 38 and 44 may be connected to temperature sensors in the catheters 24 and 26. However, it is to be understood that a single temperature sensor may be placed in only one of the catheters 24 or 26 in non-limiting embodiments. Alternatively, a patient temperature signal may be provided to the system 30 from a separate esophageal probe or rectal probe or tympanic sensor or bladder probe or other temperature probe that measures the temperature of the patient 32.

One or both catheters 24 and 26, in addition to interior supply and return lumens through which the working fluid is circulated, may also have one or more infusion lumens connectable to an IV component 46, such as a syringe or IV bag for infusing medicaments into the patient, or an instrument such as an oxygen or pressure monitor for monitoring patient parameters, etc. Although the IV component 46 as shown in FIG. 2 is connected only to the catheter 26 for clarity, it is to be understood that the IV component 46 may be connected to both catheters 24 and 26.

Figure 3:
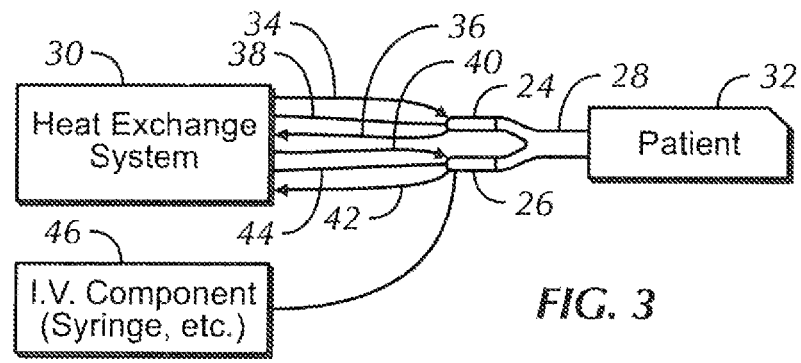
FIG. 3 is a schematic diagram of two catheters advanced in concert with each other through a Y-connector with the distal portions disposed in a patient.

The catheters of FIG. 2 are also shown in FIG. 3, with FIG. 3 showing the distal portions of the catheters 24 and 26 disposed in the patient 32. Thus, proximal portions of the catheters 24 and 26 are still fluidly connected to the heat exchange system 30 in FIG. 3, and the catheters 24 and 26 may also still be connected to the IV component 46.

It may now be further appreciated that distal portions of the catheters 24 and 26 can be positioned in concert into the same insertion site of a patient 32, typically in the vasculature of the patient 32 and more preferably in the venous system of the patient 32 such as in the inferior vena cava through a groin insertion point or the superior vena cava through a neck (jugular or subclavian) insertion point. The positioning of distal portions of the catheters 24 and 26 into the patient 32 allows for more effective and efficient heat exchange with the patient 32 than a single catheter would. Furthermore, it is to be understood that the catheters 24 and 26 may be any of the catheters described below, or may be another type of catheter not described in reference to FIGS. 4-8 in other non-limiting embodiments.

Figure 4:
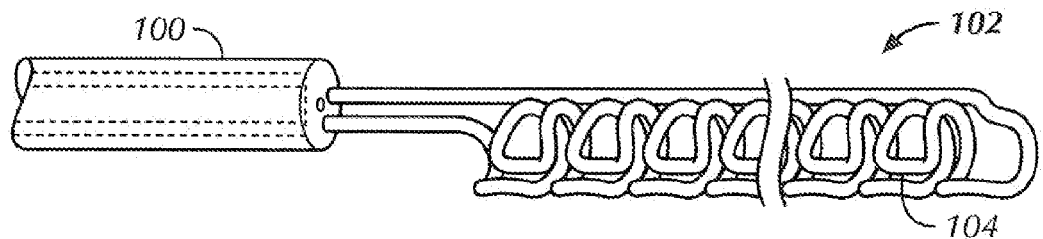
FIG. 4 is a perspective view of a first example catheter with a first example heat exchange member with plural non-straight, non-helical links, with portions of the heat exchange member broken away.

Moving on, FIGS. 4-8 show example non-limiting embodiments of the catheters 10, 24 and 26. In FIG. 4 a catheter 100 has a heat exchange segment 102 established by a series of non-straight, non-helical links 104 through which the working fluid flows serially from link to link. Further details of the construction and operation of the catheter 100 are set forth in the above-referenced U.S. Pat. No. 6,796,995.

Figure 5:
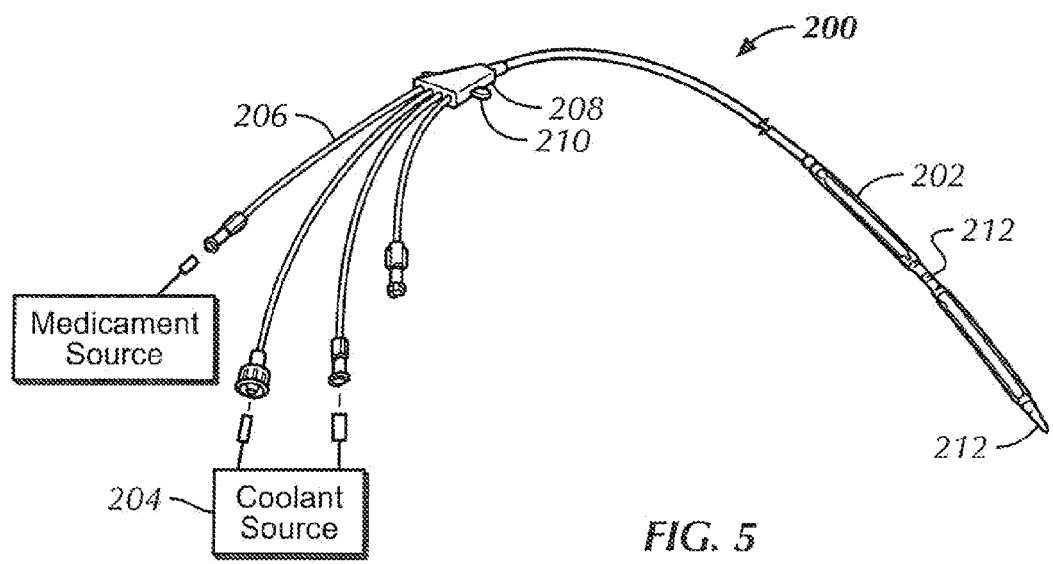
FIG. 5 is a perspective view of a second example catheter with second example heat exchange members configured as hollow balloons.

FIG. 5 shows a catheter 200 that has one or more axially-spaced cylindrical balloons 202 that carry circulating working fluid to and from a heat exchange system 204. The catheter 200 shown in FIG. 5 includes two additional infusion lumens connected to respective infusion tubes 206, with the various external tubes joining respective internal catheter lumens at a hub 208 which may be formed with suture wings 210 for suturing the hub 208 to the skin of the patient. The infusion lumens may terminate at respective axially-spaced infusion ports 212. Further details of the construction and operation of the catheter 100 are set forth in the above-referenced U.S. Pat. No. 6,368,304.

Figure 6:
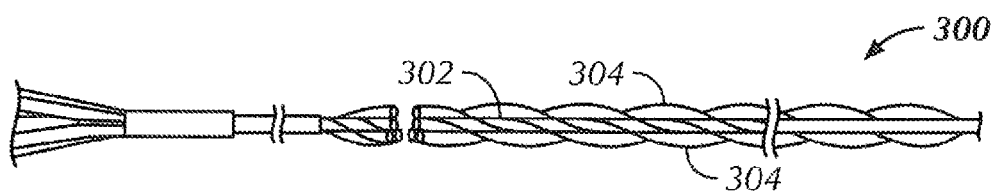
FIG. 6 is a side view of a third example catheter with a third example heat exchange member formed from a straight central supply tube surrounded by three helical return tubes.

Yet again, FIG. 6 shows a catheter 300 that has a straight central supply tube 302 surrounded by three helical return tubes 304. Further details of the construction and operation of the catheter 300 are set forth in the above-referenced U.S. Pat. Nos. 6,881,551 and 6,585,692.

Figure 7:
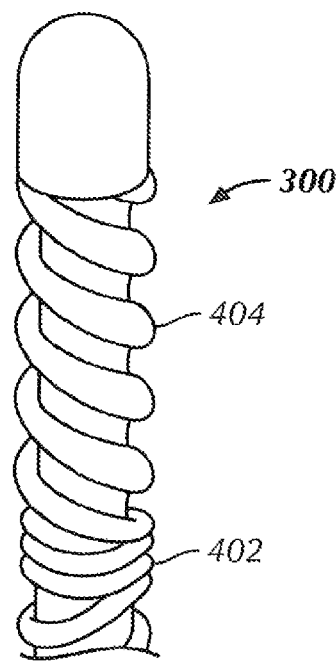
FIG. 7 is a perspective view of a fourth example catheter with fourth example heat exchange members that consist of alternating segments, along a metal tube, of bellows regions and fluted regions, with portions of the catheter broken away.
Figure 8:
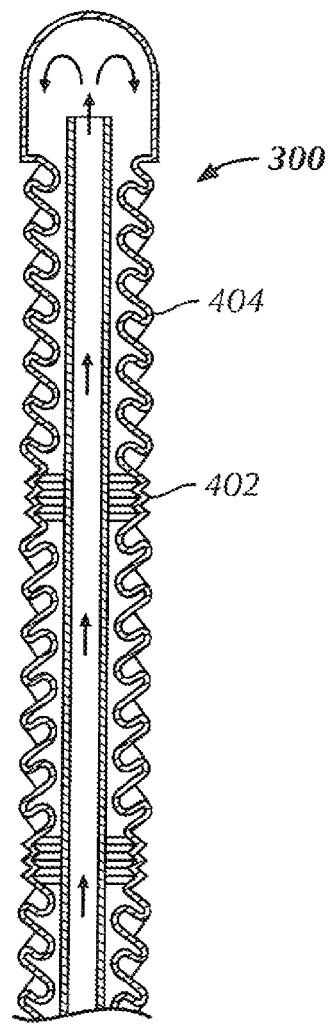
FIG. 8 is a cut-away view of the catheter shown in FIG. 6.

FIGS. 7 and 8 show a catheter 400 that may be made of a metal such as gold and that has alternating segments of bellows regions 402 and helically fluted regions 404. Further details of the construction and operation of the catheter 400 are set forth in the above-referenced U.S. Pat. Nos. 6,551,349 and 6,554,797.

While the particular SYSTEM AND METHOD FOR DOUBLED USE OF PATIENT TEMPERATURE CONTROL CATHETER is herein shown and described in detail, it is to be understood that the subject matter which is encompassed by the present invention is limited only by the claims.

What is claimed is:

1. An apparatus, comprising:
   a first elongated heat exchange catheter carrying circulating working fluid to and from a heat exchange system;
   a second elongated heat exchange catheter carrying circulating working fluid to and from the heat exchange system; and
   a connector supporting proximal portions of both catheters while distal portions of the catheters are disposed inside a patient's vasculature to exchange heat with the patient, wherein the catheters each have a heat exchange segment established by an elongated generally cylindrical balloon.

2. The apparatus of claim 1, wherein the connector is a Y-shaped connector.

3. An apparatus, comprising:
   a first elongated heat exchange catheter carrying circulating working fluid to and from a heat exchange system;
   a second elongated heat exchange catheter carrying circulating working fluid to and from the heat exchange system; and
   a connector supporting proximal portions of both catheters while distal portions of the catheters are disposed inside a patient's vasculature to exchange heat with the patient, wherein the catheters each have at least one heat exchange segment established by a series of non-straight, non-helical links through which the working fluid flows serially from link to link.

4. An apparatus, comprising:
   a first elongated heat exchange catheter carrying circulating working fluid to and from a heat exchange system;
   a second elongated heat exchange catheter carrying circulating working fluid to and from the heat exchange system; and
   a connector supporting proximal portions of both catheters while distal portions of the catheters are disposed inside a patient's vasculature to exchange heat with the patient, wherein the catheters each have at least one heat exchange segment established by a straight central supply tube surrounded by three helical return tubes.

5. An apparatus, comprising:
   a first elongated heat exchange catheter carrying circulating working fluid to and from a heat exchange system;
   a second elongated heat exchange catheter carrying circulating working fluid to and from the heat exchange system; and
   a connector supporting proximal portions of both catheters while distal portions of the catheters are disposed inside a patient's vasculature to exchange heat with the patient, wherein the catheters each have at least one heat exchange segment established by alternating segments of bellows regions and fluted regions.

6. The apparatus of claim 5, wherein the fluted regions have helical flutes.

7. A method, comprising:
   providing a first elongated heat exchange catheter carrying circulating working fluid to and from a heat exchange system;
   providing a second elongated heat exchange catheter carrying circulating working fluid to and from the heat exchange system; and
   using a connector supporting proximal portions of both catheters and disposing distal portions of the catheters inside a patient's vasculature to exchange heat with the patient, wherein the catheters have at least one heat exchange segment established by a series of non-straight, non-helical links through which the working fluid flows serially from link to link.

8. The method of claim 7, wherein the connector is a Y-shaped connector.

9. A method, comprising:
   providing a first elongated heat exchange catheter carrying circulating working fluid to and from a heat exchange system;
   providing a second elongated heat exchange catheter carrying circulating working fluid to and from the heat exchange system; and
   using a connector supporting proximal portions of both catheters and disposing distal portions of the catheters inside a patient's vasculature to exchange heat with the patient, wherein the catheters have at least one heat exchange segment established by an elongated generally cylindrical balloon.

10. A method, comprising:
    providing a first elongated heat exchange catheter carrying circulating working fluid to and from a heat exchange system;
    providing a second elongated heat exchange catheter carrying circulating working fluid to and from the heat exchange system; and
    using a connector supporting proximal portions of both catheters and disposing distal portions of the catheters inside a patient's vasculature to exchange heat with the patient, wherein the catheters have at least one heat exchange segment established by a straight central supply tube surrounded by three helical return tubes.

11. A method, comprising:
    providing a first elongated heat exchange catheter carrying circulating working fluid to and from a heat exchange system;
    providing a second elongated heat exchange catheter carrying circulating working fluid to and from the heat exchange system; and
    using a connector supporting proximal portions of both catheters and disposing distal portions of the catheters inside a patient's vasculature to exchange heat with the patient, wherein the catheters have at least one heat exchange segment established by alternating segments of bellows regions and fluted regions.

12. The method of claim 11, wherein the fluted regions have helical flutes.

13. A system, comprising:
plural elongated heat exchange catheters carrying circulating working fluid to and from a heat exchange system; and
a connector supporting proximal portions of the catheters while distal portions of the catheters are disposed inside a patient's vasculature to exchange heat with the patient, wherein the catheters have at least one heat exchange segment established by a straight central supply tube surrounded by three helical return tubes.

14. A system, comprising:
plural elongated heat exchange catheters carrying circulating working fluid to and from a heat exchange system; and
a connector supporting proximal portions of the catheters while distal portions of the catheters are disposed inside a patient's vasculature to exchange heat with the patient, wherein the catheters have at least one heat exchange segment established by an elongated generally cylindrical balloon.

15. A system, comprising:
plural elongated heat exchange catheters carrying circulating working fluid to and from a heat exchange system; and
a connector supporting proximal portions of the catheters while distal portions of the catheters are disposed inside a patient's vasculature to exchange heat with the patient, wherein the catheters have at least one heat exchange segment established by a series of non-straight, non-helical links through which the working fluid flows serially from link to link.

16. A system, comprising:
plural elongated heat exchange catheters carrying circulating working fluid to and from a heat exchange system; and
a connector supporting proximal portions of the catheters while distal portions of the catheters are disposed inside a patient's vasculature to exchange heat with the patient, wherein the catheters have at least one heat exchange segment established by alternating segments of bellows regions and fluted regions.

17. The system of claim 16, wherein the fluted regions have helical flutes.

* * * * *